United States Patent [19]

Miles

[11] 4,456,017

[45] Jun. 26, 1984

[54] COIL SPRING GUIDE WITH DEFLECTABLE TIP

[75] Inventor: Marshall Miles, Miami, Fla.

[73] Assignee: Cordis Corporation, Miami, Fla.

[21] Appl. No.: 443,204

[22] Filed: Nov. 22, 1982

[51] Int. Cl.³ .......................................... A61M 25/00
[52] U.S. Cl. ..................................... 128/772; 604/95; 604/227
[58] Field of Search ........................ 128/772, 756–757, 128/657; 604/95, 227

[56] References Cited

U.S. PATENT DOCUMENTS

| 1,832,533 | 11/1931 | Creasy | 604/227 |
|---|---|---|---|
| 2,847,990 | 8/1958 | Ayre | 128/756 |
| 3,452,742 | 7/1969 | Muller | 128/772 |
| 3,521,620 | 7/1970 | Cook | 604/95 |
| 3,749,086 | 7/1973 | Kline et al. | 128/772 |
| 3,789,841 | 2/1974 | Antoshkiw | 128/772 |
| 3,841,308 | 10/1974 | Tate | 128/772 |
| 3,973,556 | 8/1976 | Fleischhacker et al. | 128/772 |

FOREIGN PATENT DOCUMENTS

| 503064 | 7/1930 | Fed. Rep. of Germany | 604/227 |
|---|---|---|---|
| 43-27685 | 11/1968 | Japan | 604/95 |

Primary Examiner—Richard J. Apley
Assistant Examiner—Harry Macey
Attorney, Agent, or Firm—Henry W. Collins; Thomas R. Vigil

[57] ABSTRACT

The coil spring guide (12) is particularly adapted for use in connection with the insertion of a catheter into a vessel of a body. The guide (12) comprises a coil spring (14), a core wire (16) within the coil spring (14) extending the length of the coil spring (14) and a head member (20). A thin core wire extension (18) connects the distal end of the core wire (16) to the head member (20) and the coil spring (14) and head member (20) are covered with a sheath (26). The coils or turns of the coil spring (14) in the distal end portion of the coil spring (14) are spaced from each other. A mechanism (58, 70; 60, 80) is provided at the proximal end (54) of the coil spring guide (12) for causing movement of the core wire (16) relative to the coil spring (14). The core wire extension (18) is eccentrically fixed to the back side (22) of the head member (20) adjacent to a lateral side (28) thereof whereby rearward movement of the core wire (16) causes compression of the distal end portion of the coil spring (14) and lateral movement thereof to one side of the center line of the coil spring (14) and in a direction outwardly from the lateral side (28) of the head member (20) to which the core wire extension is fixed.

6 Claims, 4 Drawing Figures

COIL SPRING GUIDE WITH DEFLECTABLE TIP

BACKGROUND OF THE INVENTION

1. Field of the Invention

The present invention is directed to a coil spring guide with a deflectable tip such as are used in connection with the insertion of a catheter into a vessel of a body. Such coil spring guides are often referred to as angiographic guide wires.

2. Description of the Prior Art

Heretofore coil spring guides or guide wires have been widely used for facilitating the insertion of a catheter into a vessel. In some applications, the coil spring guide with a rounded tip is inserted into a vessel and then the catheter is slipped about the coil spring guide until it is in place and then the guide is retracted from the vessel. In another application, the coil spring guide is first inserted into the catheter tubing with the tip of the guide extending beyond the distal end of the catheter tubing. Then, this assembly is inserted into a vessel with the rounded tip of the coil spring guide facilitating movemement of the guide and catheter tubing into the vessel without puncturing the vessel. Then, once in place, the coil spring guide is retracted leaving the catheter in the vessel.

It is desirable in using such coil spring guides to provide some means for deflecting the tip of the guide to facilitate movement of the guide around or through a curved path in the vessel.

Heretofore there have been a number of proposals for different tip constructions which will provide a deflectable tip in a coil spring guide or guide wire.

Examples of previously proposed coil spring guides including guides with a particular tip construction to facilitate deflecting of the tip are disclosed in the following U.S. patents:

| U.S. PAT. NO. | PATENTEE |
|---|---|
| 3,452,740 | Muller |
| 3,452,742 | Muller |
| 3,521,620 | Cook |
| 3,528,406 | Jeckel et al. |
| 3,547,103 | Cook |
| 3,841,308 | Tate |
| 3,973,556 | Fleischhacker et al. |

The Muller U.S. Pat. No. 3,452,740 discloses an unsheathed coil spring guide manipulator having a core wire with an extension of the core wire extending to a cap or plug at the distal end of a spring coil. The turns of the coil on one side of the spring guide have the side edges of the coils cut away so as to provide a greater space between the respective turns on the side of the spring coil. As a result, pulling of the core wire rearwardly will cause bending of the core wire extension as the coil turns with the sides cut away are compressed against one another. In this way, the tip is caused to deflect.

The Muller U.S. Pat. No. 3,452,742 discloses an unsheated curvable spring guide having the same tip construction as the coil spring in the Muller U.S. Pat. No. 3,452,740 to facilitate deflection of the tip.

The Cook U.S. Pat. No. 3,521,620 discloses a coil spring guide with a bendable tip. The coil spring guide is unsheathed and has a tip member at the distal end of the spring coil. The turns of the coil in the distal end portion of the coil are spaced apart from each other. Two wires are situated within the lumen or cylindrical envelope formed by the coil spring guide and extend to the tip member on diametrically opposite sides of the cylindrical envelope so that one wire is fixed to one lateral edge of the tip member and the other wire is fixed to the opposite lateral edge of the tip member. The first wire extends to the proximal end of the distal end portion of the coil spring and is held in place by a lump of solder which extends between adjacent coil turns of the coil spring guide at the proximal end of the distal end portion of the coil spring guide. The other or second wire extends all the way back to the proximal end of the coil spring guide.

In the use of the coil spring guide disclosed in the Cook U.S. Pat. No. 3,521,620, retraction of the wire on one side of the cylindrical envelope will cause the tip to be pulled rearwardly. However, the first wire on the other side of the cylindrical envelope is prevented from moving because it is fixed at one end to the tip member and at the other end to the solder plug which engages turns of the coil spring. This results in bending of the first wire which is under compression and resulting bending of the distal end portion or tip of the coil spring guide.

The Jeckel et al. U.S. Pat. No. 3,528,406 discloses an unsheated flexible spring guide tip which has two core wires one of which is thinner than the other with the thinner wire extending to and being fixed to a plug at the distal end of the tip and both the thinner wire and thicker wire being fixed to the proximal end of the spring guide and with the thicker wire extending only to the beginning of the tip so that the tip is more flexible.

In another embodiment disclosed in the Jeckel et al. U.S. Pat. No. 3,528,406, the core wire has a reduced-in-diameter section at the tip thereof which extends from the thicker portion of the core wire to the back side of the end plug and is fixed thereto.

The Cook U.S. Pat. No. 3,547,103 discloses an unsheathed coil spring guide which has a predetermined "J" set in the tip portion thereof. A core wire extends within the coil spring to the center back side of the tip member and is fixed thereto. The "J" shape of the tip portion is straightened by stretching the proximal end of the coil spring guide thereby compressing the tip portion of the coil spring guide to bring it from a curved "J" shape to a straight position.

The Tate U.S. Pat. No. 3,841,308 discloses a distally valved catheter device which includes a coil spring having the turns of the coil spring at the distal end thereof spaced apart. A coating or sheath covers the coil spring and the portion of the coating at the tip has ports therein. A closure or tip member is located at the distal end of the coil spring and has a stylet connected to the back side thereof and extending within the coil spring. Movement of the stylet will cause compression of the coil spring at the distal tip thereby to crumple the coating at the tip in an accordian-like fashion to close the ports therein.

The Fleischhaker et al. U.S. Pat. No. 3,973,556 discloses a smoothened coil spring wire guide where a coil spring wire is coated with a plastic coating such as Teflon TM and then material is removed to provide a smoothened surface partially defined by the machine Teflon TM and partially defined by the machined outer side surfaces of the turns of the coil spring wire. In this way, when the coil spring is bent, the Teflon TM or other plastic material provides a seal between the expanded turns so that the body fluids and material cannot enter into the lumen or cylindrical envelope defined by the coil spring wire guide. There is no disclosure in this patent as to how the coil spring wire guide would be bent.

As will be described in greater detail hereinafter, the coil spring guide with deflectable tip of the present invention differs from the previously proposed coil spring guides by providing for the eccentric connection of a reduced-in-diameter distal end portion of a core wire to a head or plug member at the distal end of a coil spring guide where the turns of the coil spring at the distal end portion thereof are spaced apart and wherein the coil spring guide and head or plug member are encased within a sheath. In this construction of a coil spring guide, the eccentric mounting of a reduced-in-diameter end portion of a core wire, namely connecting the distal end thereof to the back side of the head member adjacent one side thereof will result in deflection of the distal end portion of the coil spring guide outwardly from that lateral side of the head member to which the core wire is attached when the core wire is moved rearwardly.

SUMMARY OF THE INVENTION

According to the invention there is provided a coil spring guide for use in connection with the insertion of a catheter into a vessel of a body, said guide comprising a coil spring, a core wire within said coil spring extending the length of said coil spring, a head member, means for coupling said head member to the distal end of said core wire, the coils in the distal end portion of said coil spring being spaced from each other and the distal end of said coil spring engaging the back side of said head member, means coupled to the proximal end of said coil spring and of said core wire for causing movement of said core wire relative to said coil spring, a sheath of smooth plastic material completely surrounding said coil spring and having a closed distal end completely covering said head member, said coupling means including a distal, reduced-in-cross-section core wire portion fixed to and extending from said core wire to said back side of said head member and fixed to said back side of said head member at and adjacent to a lateral side thereof whereby rearward movement of said core wire causes compression of said distal end portion of said coil spring and lateral movement thereof to one side of the center line of said coil spring and in a direction outwardly from the lateral side of said head member to which said distal core wire portion is fixed.

DESCRIPTION OF THE PREFERRED EMBODIMENT

Figure 1:
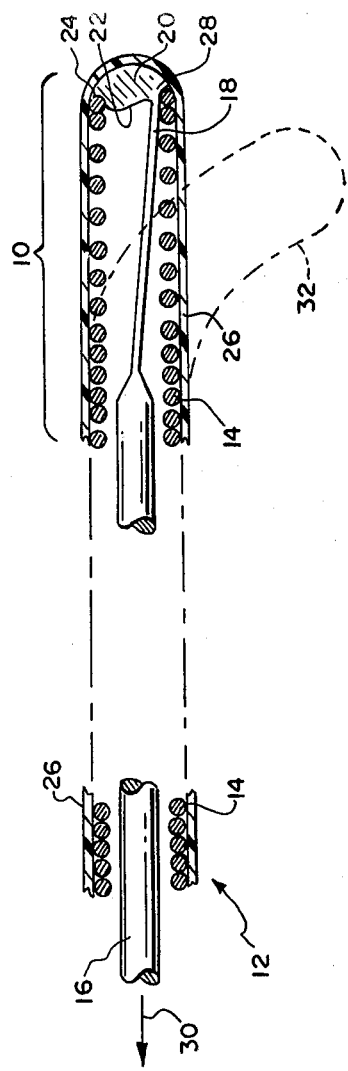
FIG. 1 is a fragmentary sectional view of the distal end portion of the coil spring guide of the present invention.

Referring now to FIG. 1 there is illustrated therein a distal end portion 10 of a coil spring guide 12. As shown, the coil spring guide 12 includes a coil spring 14 the turns or coils of which at the distal end portion 10 are spaced apart from one another.

Within the coil spring 14 is a core wire 16 which has a reduced-in-diameter distal end portion 18 which extends from the thicker core wire 16 to a head or plug member 20 at the distal end of the coil spring guide 12. This head or plug member 20 has a back side 22 which engages the distal end or last turn or coil 24 of the coil spring 14.

Also as shown in FIG. 1, the coil spring 14 and the head member 20 are encased in a sheath 26 made of a smooth plastic material such as tetrafluoroethylene sold under the trademark Teflon.

In accordance with one aspect of the present invention, the reduced-in-diameter distal end portion 18 of the core wire 16 extends from the core wire 16 to the back side 22 of the head member 20 and is fixed thereto at and adjacent to a lateral side 28 of the head member 20. With this construction of the distal end portion 10 of the coil spring guide 12 rearward movement of the core wire 16 as indicated by the arrow 30 will cause the spaced apart coils of the coil spring 14 in the distal end portion 10 to be compressed and the compression will bear against the back side 22 of the head member 20 and because of the eccentric connection of the distal end portion 18 of the core wire 16, the distal end portion or tip 10 of the coil spring guide 12 will be deflected outwardly from the side 28 of the head member 20 to a curved or bent position generally indicated by the reference numeral 32.

In other words, the eccentric connection of the reduced-in-diameter distal end portion 18 of the core wire 16 to the back side 22 of the head member 20 results in a deflection outwardly from the side 28 of the head member 20 when the coil spring 14 within the sheath 26 at the distal end portion 10 is compressed.

Figure 2:
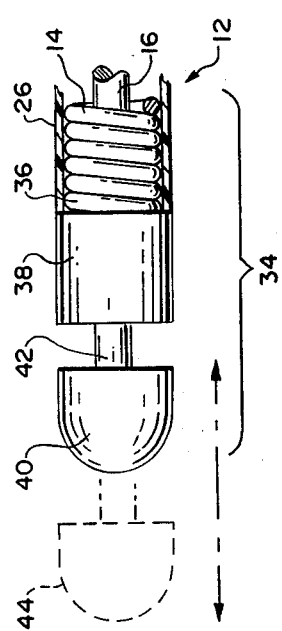
FIG. 2 is a fragmentary view partially in cross section of the proximal end of the coil spring guide of the present invention.

In FIG. 2 is shown the proximal end portion 34 of the coil spring guide 12. Here the proximal end turn 36 of the coil spring 14 is fixed to a hub 38 which can be grasped by an operator to hold the proximal end against movement. Then one can grip a grippable member 40 which is fixed to the proximal end 42 of the core wire 16 which extends through the hub 38 and move it rearwardly to the position shown in phantom and identified by the reference numeral 44 thereby to cause the distal end 10 of the coil spring guide 12 to be deflected as shown in phantom and identified by reference numeral 32.

Figure 3:
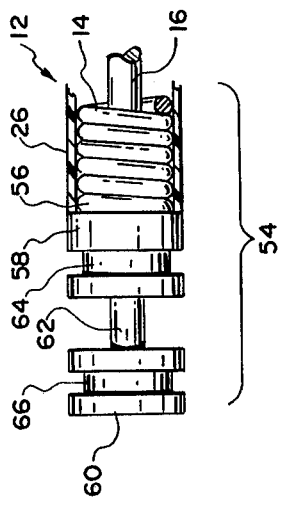
FIG. 3 is a fragmentary view partially in cross section of another embodiment of the proximal end of the coil spring guide shown in FIG. 2.

In accordance with another aspect of the present invention, the coil spring guide 12 is formed with a proximal end 54 having the construction shown in FIG. 3. Here the proximal end 54 has a proximal end turn 56 of the coil 14 fixed to a hub 58 which has a diameter that is no greater than the diameter of the sheath 26.

The proximal end portion 54 of the coil spring guide 12 further includes a short cylindrical grippable member 60 which is connected to the proximal end 62 of the core wire 16. The grippable member 60 also has a diameter no greater than the diameter of the sheath 26.

With this construction of the hub 58 and the grippable member 60, the proximal end 54 of the coil spring guide 12 can be easily received within a catheter tubing (not shown) to permit and facilitate relative movement between the coil spring guide 12 and a catheter tubing.

In accordance with a further aspect of the present invention, the hub 58 is provided with an annular groove 64 and the short cylindrical grippable member 60 is provided with a similar annular groove 66.

Figure 4:
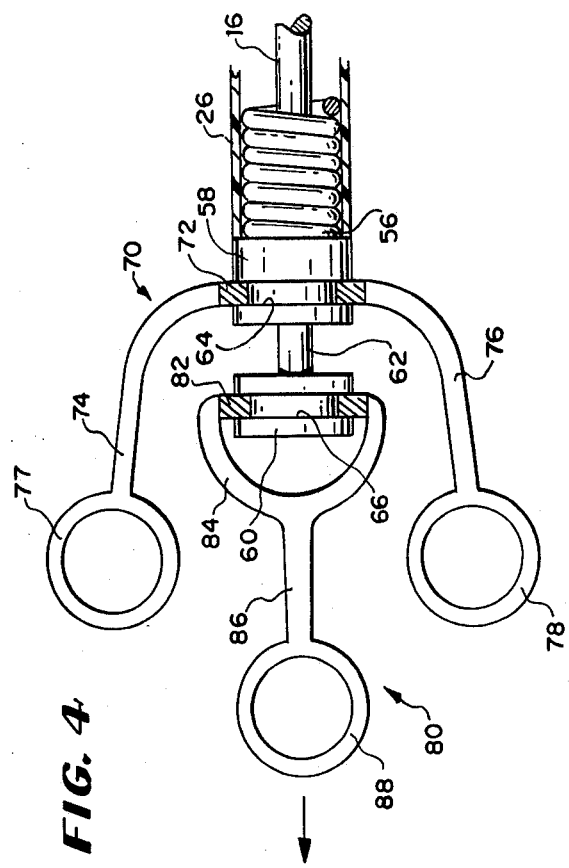
FIG. 4 is a fragmentary view partially in section of the proximal end of the coil spring guide as shown in FIG. 3 and shows two handle members, one detachably connected to a hub at the proximal end of the coil spring and the other detachably connected to a grippable member at the proximal end of the core wire which extends into and through the coil spring.

As best shown in FIG. 4, the annular groove 64 in the hub 58 facilitates and provides a means for detachably mounting a first handle 70 to the hub 58. The handle 70 is in the form of a U-shaped yoke 70 having a center ring 72 at the bight of the yoke with a portion of the ring cut away to form a C-shaped configuration which is snap-fittingly received in the annular groove 64. Then, two diametrically opposite legs 74 and 76 extend rearwardly from the ring 72 and each have a finger receiving ring 77 and 78 respectively by which an operator can grip the handle 70 with two fingers of one hand.

A second handle 80 is adapted to be detachably received in the slot 66. Handle 80 includes a ring 82 having a portion cut away to provide a C-shaped configuration that is received in the slot 66. The C-shaped ring 82 is connected by a yoke 84 to an arm 86 having a finger receivig ring 88 at the proximal end thereof.

With this construction the handle 70 can be detachably connected to the hub 58 and the handle 80 can be detachably connected to the grippable member 60. Then, an operator can grip by means of the finger receiving rings 77 and 78 the handle 70 to hold the hub 58 stationary while he grips the other handle 80 by inserting a finger through the ring 88 to pull the core wire 16 rearwardly to cause deflection of the distal end portion 10 of the coil spring guide 12.

Then, after the coil spring guide 12 has been inserted as desired into a vessel with a catheter tubing thereon or with a catheter tubing inserted afterward thereon, the handles 70 and 80 can be detached from the hub 58 and the grippable member 60 to facilitate relative movement between the coil spring guide 12 and a catheter tubing received thereon or to be received thereover.

From the foregoing description it is apparent that the coil spring guide 12 of the present invention provides a number of advantages, some of which have been described above and other of which are inherent in the invention. In particular, the coil spring guide 12 can be used as an angiographic guidewire and the construction of the tip portion 10 facilitates deflection of the tip portion 10 of the coil spring guide 12. Also the construction of the proximal end portion 54 and the provision of the detachable handles 70 and 80 enable one to manipulate the coil spring guide 12 and particularly the tip portion 10 thereof followed by detachment of the handles 70 and 80 to permit relative movement between the coil spring guide 12 and a catheter tubing received thereover.

Also it will be apparent to those skilled in the art that modifications can be made to the coil spring guide 12 of the present invention without departing from the teachings of the invention. Accordingly, the scope of the invention is only to be limited as necessitated by the accompanying claims.

I claim:

1. A coil spring guide for use in connection with the insertion of a catheter into the vessel of a body, said guide comprising a coil spring, a core wire within said coil spring extending the length of said coil spring, a head member, means for coupling said head member to the distal end of said core wire, the coils in the distal end portion of said coil spring being spaced from each other and the distal end of said coil spring engaging the backside of said head member, means coupled to the proximal end of said coil spring and of said core wire for causing movement of said core wire relative to said coil spring, a sheath of smooth plastic material completely surrounding said coil spring and having a closed distal end completely covering said head member, said coupling means including a distal, reduced-in-cross-section core wire portion fixed to and extending from said core wire to said back side of said head member and fixed to said back side of said head member at and adjacent to a lateral side thereof whereby rearward movement of said core wire causes compression of said distal end portion of said coil spring and lateral movement thereof to one side of said center line of said coil spring and in a direction outwardly from the lateral side of said head member to which said distal core wire portion is fixed.

2. The coil spring guide of claim 1 wherein said means for causing relative movement include a hub connected to the proxmal end of said coil spring and a grippable handle member connected to the proximal end of said core wire which extends through said hub.

3. The coil spring guide of claim 1 wherein said means for causing relative movement include a hub connected to the proximal end of said coil spring, said hub having a diameter no greater than the outer diameter of said sheath, and a grippable member connected to the proximal end of said core wire which extends through said hub, said grippable member having a diameter no greater than the diameter of said sheath.

4. The coil spring guide of claim 3 wherein said means for causing relative movement further comprise a first handle member detachably connectable to said hub and a second handle member detachably connected to said grippable member.

5. The coil spring guide of claim 4 wherein said hub has an annular slot therein and said first handle member includes a yoke having a ring at the bight of the yoke with a portion of said ring cut away to form a C-shaped configuration which is snapfittingly engagable in said annular slot and having first and second legs extending from said ring diametrically opposite each other, the outer end of each leg having a finger engageable formation.

6. The coil spring guide of claim 4 wherein said grippable member has an annular slot therein and said second handle member includes a yoke having a finger engageable formation at one end thereof and a ring at the other end thereof with a portion of said ring cut away to form a C-shaped configuration which is snapfittingly engageable in said annular slot.

* * * * *